United States Patent
Cogley

(10) Patent No.: US 10,736,783 B1
(45) Date of Patent: Aug. 11, 2020

(54) FLUID EAR MEDICATION DISPENSER SYSTEM

(71) Applicant: Thomas Paul Cogley, Pinellas Park, FL (US)

(72) Inventor: Thomas Paul Cogley, Pinellas Park, FL (US)

( * ) Notice: Subject to any disclaimer, the term of this patent is extended or adjusted under 35 U.S.C. 154(b) by 14 days.

(21) Appl. No.: 16/276,812

(22) Filed: Feb. 15, 2019

Related U.S. Application Data

(60) Provisional application No. 62/631,742, filed on Feb. 17, 2018.

(51) Int. Cl.
*A61F 11/00* (2006.01)
*A61M 31/00* (2006.01)

(52) U.S. Cl.
CPC ............. *A61F 11/00* (2013.01); *A61M 31/00* (2013.01); *A61M 2210/0662* (2013.01)

(58) Field of Classification Search
CPC ............... A61F 11/00; A61M 31/00; A61M 2210/0662; A61B 2017/00787; A61B 17/22047; A61B 17/3482; A61B 17/3484; A61B 17/3488
See application file for complete search history.

(56) References Cited

U.S. PATENT DOCUMENTS

| | | | | |
|---|---|---|---|---|
| 10,166,146 | B2* | 1/2019 | Mitchnick | A61F 11/00 |
| 2008/0154183 | A1* | 6/2008 | Baker | A61M 1/0058 |
| | | | | 604/28 |
| 2008/0262468 | A1* | 10/2008 | Clifford | A61M 31/00 |
| | | | | 604/501 |
| 2010/0198135 | A1* | 8/2010 | Morriss | A61N 1/0526 |
| | | | | 604/21 |
| 2018/0296812 | A1* | 10/2018 | Boone | A61M 31/00 |

* cited by examiner

*Primary Examiner* — Nathan R Price
*Assistant Examiner* — John A Doubrava

(57) ABSTRACT

A dispensing assembly has a forward positioning section, an intermediate storage section, and a rearward operational section. The forward positioning section has an exterior end in a semi-spherical configuration with a forward passageway. The intermediate storage section has a storage chamber for fluid medication whereby the fluid medication may be fed through the forward passageway and out of the exterior end of the forward positioning section. A door in the intermediate storage section facilitates the addition of fluid medication. A piston is in the intermediate storage section. The rearward operational section drives the piston axially within the storage chamber whereby fluid medication in the storage chamber may be fed through the forward passageway and out of the exterior end of the positioning section into the ear of the pet.

1 Claim, 3 Drawing Sheets

FLUID EAR MEDICATION DISPENSER SYSTEM

BACKGROUND OF THE INVENTION

Field of the Invention

The present invention relates to a fluid ear medication dispenser system and more particularly pertains to holding fluid medication adjacent to an ear canal of a pet and for accurately administering the fluid medication into the ear. The holding and administering area done in a safe, convenient, and economical manner.

Description of the Prior Art

The use of dispensers for ear medication for pets of known designs and configurations is known in the prior art. More specifically, dispensers for ear medication for pets of known designs and configurations previously devised and utilized for the purpose of administering ear medication to pets are known to consist basically of familiar, expected, and obvious structural configurations, notwithstanding the myriad of designs encompassed by the crowded prior art which has been developed for the fulfillment of countless objectives and requirements.

While these devices fulfill their respective, particular objectives and requirements, they do not describe a fluid ear medication dispenser system that allows holding fluid medication adjacent to an ear canal of a pet and for accurately administering the fluid medication into the ear. The holding and administering area done in a safe, convenient, and economical manner.

In this respect, the fluid ear medication dispenser system according to the present invention substantially departs from the conventional concepts and designs of the prior art, and in doing so provides an apparatus primarily developed for the purpose of holding fluid medication adjacent to an ear canal of a pet and for accurately administering the fluid medication into the ear. The holding and administering area done in a safe, convenient, and economical manner.

Therefore, it can be appreciated that there exists a continuing need for a new and improved fluid ear medication dispenser system which can be used for holding fluid medication adjacent to an ear canal of a pet and for accurately administering the fluid medication into the ear. The holding and administering area done in a safe, convenient, and economical manner. In this regard, the present invention substantially fulfills this need.

SUMMARY OF THE INVENTION

In view of the disadvantages inherent in the known types of dispensers for ear medication for pets of known designs and configurations now present in the prior art, the present invention provides an improved fluid ear medication dispenser system. As such, the general purpose of the present invention, which will be described subsequently in greater detail, is to provide a new and improved fluid ear medication dispenser system and method which has all the advantages of the prior art and none of the disadvantages.

To attain this, from a broad perspective, the present invention essentially comprises a dispensing assembly having a forward positioning section, an intermediate storage section, and a rearward operational section. The forward positioning section has an exterior end in a semi-spherical configuration with a forward passageway. The intermediate storage section has a storage chamber for fluid medication whereby the fluid medication may be fed through the forward passageway and out of the exterior end of the forward positioning section. A door in the intermediate storage section facilitates the addition of fluid medication. A piston is in the intermediate storage section. The rearward operational section drives the piston axially within the storage chamber whereby fluid medication in the storage chamber may be fed through the forward passageway and out of the exterior end of the positioning section into the ear of the pet.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved fluid ear medication dispenser system which has all of the advantages of the prior art dispensers for ear medication for pets of known designs and configurations and none of the disadvantages.

It is another object of the present invention to provide a new and improved fluid ear medication dispenser system which may be easily and efficiently manufactured and marketed.

It is a further object of the present invention to provide a new and improved fluid ear medication dispenser system which is of a durable and reliable constructions.

An even further object of the present invention is to provide a new and improved fluid ear medication dispenser system which is susceptible of a low cost of manufacture with regard to both materials and labor, and which accordingly is then susceptible of low prices of sale to the consuming public, thereby making such fluid ear medication dispenser system economically available to the buying public.

Lastly, it is an object of the present invention to provide a fluid ear medication dispenser system for holding fluid medication adjacent to an ear canal of a pet and for accurately administering the fluid medication into the ear. The holding and administering area done in a safe, convenient, and economical manner.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figures 1, 2:
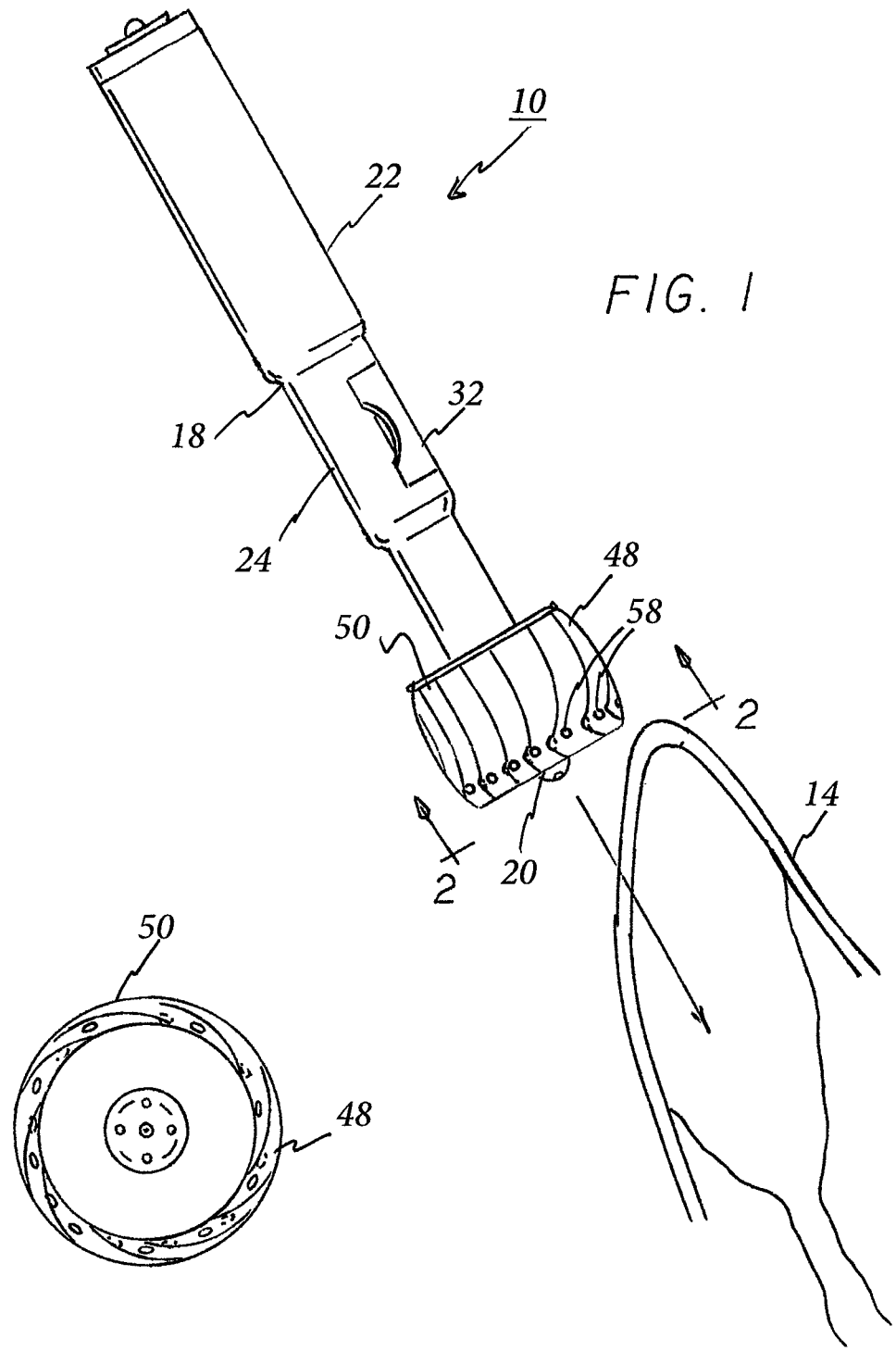
FIG. 1 is a front elevational view of a fluid ear medication dispenser system constructed in accordance with the principles of the present invention, the system shown prior to positioning for use.
FIG. 2 is a bottom view of the system taken along line 2-2 of FIG. 1.

With reference now to the drawings, and in particular to FIG. 1 thereof, the preferred embodiment of the new and improved fluid ear medication dispenser system embodying the principles and concepts of the present invention and generally designated by the reference numeral 10 will be described.

The present invention, the fluid ear medication dispenser system 10 is comprised of a plurality of components. In their broadest context the invention is a dispensing assembly having a forward positioning section, a intermediate storage section, and a rearward operational section. Such components are individually configured and correlated with respect to each other so as to attain the desired objective.

From a specific perspective, the invention of the present application is a fluid ear medication dispenser system 10 for holding fluid medication 12 adjacent to an ear canal 14 of a pet and for accurately administering the fluid medication into the ear. The holding and the administering are done in a safe, convenient, and economical manner.

A dispensing assembly 18 is first provided. The dispensing assembly has a forward positioning section 20, a rearward operational section 22, and an intermediate storage section 24 between the forward positioning section and the rearward operational section.

Figure 3:
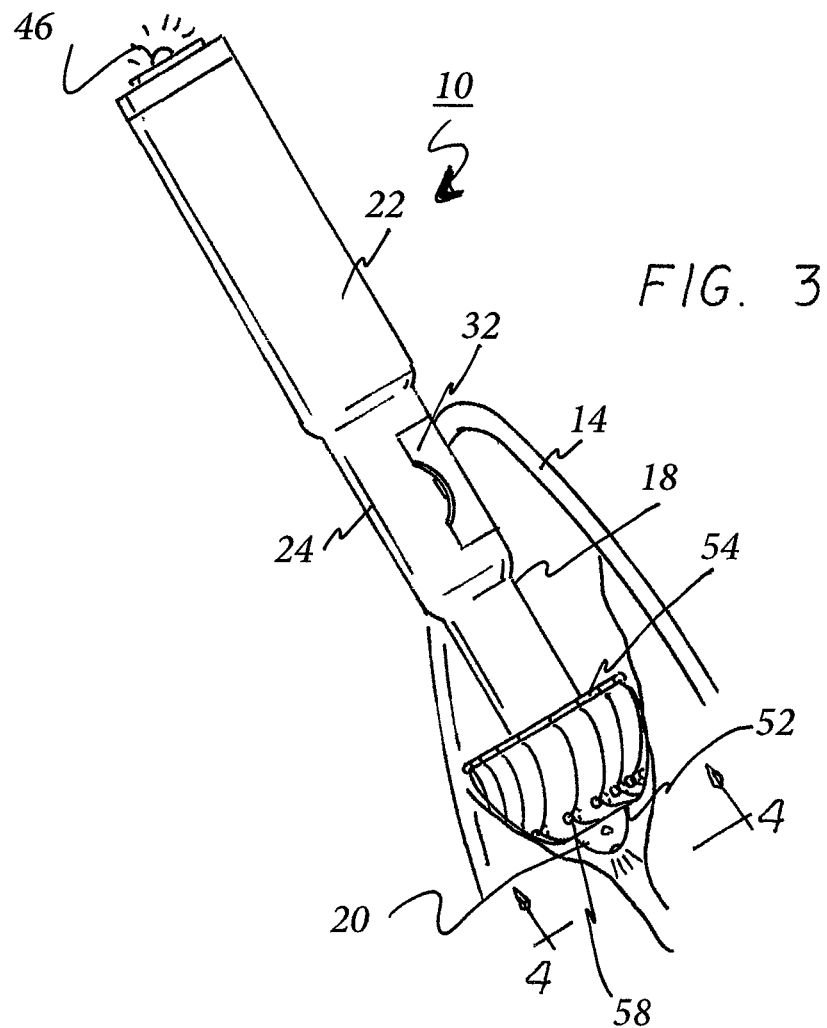
FIG. 3 is a front elevational view of similar to FIG. 1 but with the system shown after positioning for use.
Figure 4:
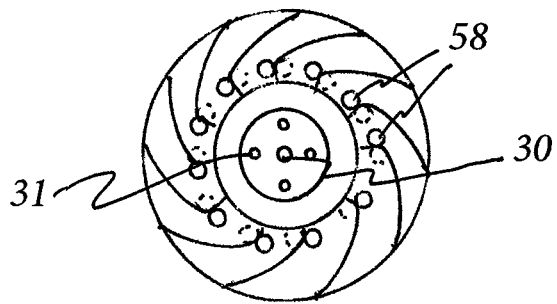
FIG. 4 is a bottom view of the system taken along line 4-4 of FIG. 3.
Figure 5:
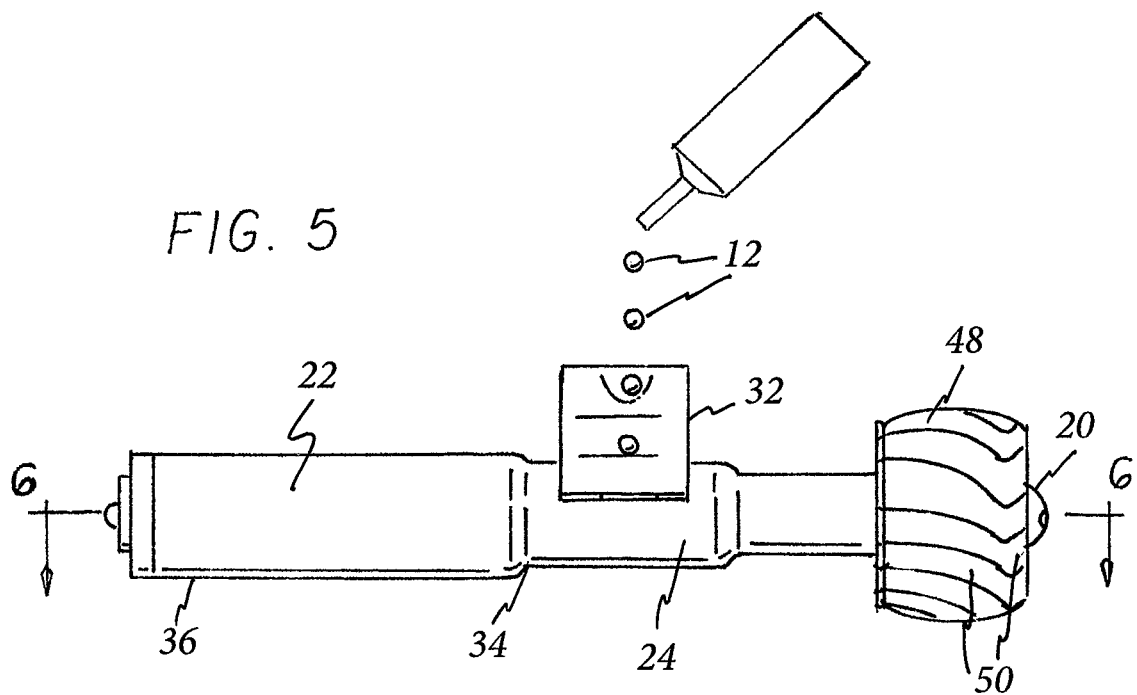
FIG. 5 is a front elevational view of similar to FIG. 1 but with the door open for receiving medicine for administering to a pet.
Figure 6:
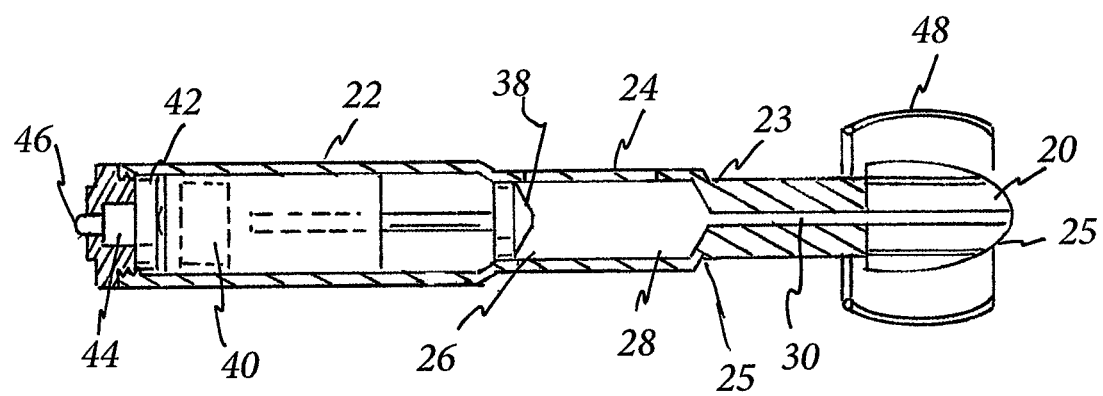
FIG. 6 is a cross sectional view taken along line 6-6 of FIG. 5.

The forward positioning section 20 is tubular with a first exterior diameter and first interior diameter. The forward positioning section has an interior end 23 and an exterior end 25. The exterior end has a semi-spherical configuration positionable in contact with an outer ear canal of the pet. Note FIG. 3. A forward passageway 30 extends through the forward positioning section.

The intermediate storage section 24 is tubular with a second exterior diameter greater than the first exterior diameter and with a second interior diameter greater than the first interior diameter. The intermediate storage section has an interior end 26 and an exterior end 28 and with a storage chamber there between. The interior end of the intermediate storage section is integrally formed with the exterior end of the forward positioning section with the forward passageway 30. In this manner, the fluid medication 12 in the storage chamber may be fed through the forward passageway and out of the exterior end of the forward positioning section. Air exhaust passageways 31 parallel with the forward passageway allow air relief rearwardly. A door 32 is provided in the intermediate storage section for facilitating the addition of a prescribed amount of fluid medication 12 to the storage chamber.

The rearward operational section 22 is tubular with a third exterior diameter greater than the second exterior diameter and with a third interior diameter greater than the second interior diameter. The rearward operational section has an interior end 34 and an exterior end 36 with an operational chamber there between. The exterior end of the rearward operational section is integrally formed with the interior end of the intermediate storage section. A piston 38 is axially reciprocable within the storage chamber whereby fluid medication in the storage chamber may be fed through the forward passageway and out of the exterior end of the positioning section into the ear of the pet. A motor 40 within the operational chamber drives the piston to dispense the fluid medication. An operator controlled processor 42 is provided for driving the piston at a rate dictated by the fluid medication. A source of potential 44 is provided for powering the motor and the processor. An illuminating ON/OFF button 46 is also provided.

Lastly, a positioner enhancer 48 is provided. The positioner enhancer is formed of a plurality of similarly configured imperforate plates 50 with lower ends 52 and upper ends 54. The lower ends are pivotally coupled to the forward positioning section. The upper ends are adapted to be pivoted to an increased diameter. The lower ends are adapted to be pivoted to a decreased diameter, by contact with the ear canal, for abating the passage of fluid medication to above the position enhancer. Electrically conductive contacts 58 on each of the imperforate plates are adapted to contact each other and close an electrical circuit to illuminate the ON/OFF button 46 to indicate it is ready to activate the system and drive the piston.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An ear medication dispenser system (10) for holding fluid medication (12) adjacent to an ear canal (14) of a pet and for accurately administering the fluid medication into the ear canal, the holding and the administering being done in a safe, convenient, and economical manner, the system comprising, in combination:

a dispensing assembly (18) having a forward positioning section (20) and a rearward operational section (22) and an intermediate storage section (24) between the forward positioning section and the rearward operational section;

the forward positioning section (20) being tubular with a first exterior diameter and first interior diameter, the forward positioning section having an interior end (22) and an exterior end (25), the exterior end having a semi-spherical configuration positionable in contact with an outer ear canal of the pet, a forward passageway (30) extending through the forward positioning section;

the intermediate storage section (24) being tubular with a second exterior diameter greater than the first exterior diameter and with a second interior diameter greater than the first interior diameter, the intermediate storage section having an interior end (26) and an exterior end (28) and with a storage chamber there between, the interior end of the intermediate storage section being integrally formed with the exterior end of the forward positioning section with the forward passageway (30) whereby the fluid medication (12) in the storage chamber may be fed through the forward passageway and out of the exterior end of the forward positioning section, air exhaust passageways (31) parallel with the forward passageway to allow air relief rearwardly, a door (32) in the intermediate storage section for facilitating the addition of a prescribed amount of fluid medication (12) to the storage chamber;

the rearward operational section (22) being tubular with a third exterior diameter greater than the second exterior diameter and with a third interior diameter greater than the second interior diameter, the rearward operational section having an interior end (34) and an exterior end (36) with an operational chamber there between, the exterior end of the rearward operational section being integrally formed with the interior end of the intermediate storage section, a piston (38) axially reciprocable within the storage chamber whereby fluid medication in the storage chamber may be fed through the forward passageway and out of the exterior end of the positioning section into the ear of the pet, a motor (40) within the operational chamber for driving the piston to dispense the fluid medication, an operator controlled processor (42) for driving the piston at a rate dictated by the fluid medication, a source of potential (44) for powering the motor and the processor, and an illuminating ON/OFF button (46); and a positioner enhancer (48), the positioner enhancer formed of a plurality of similarly configured imperforate plates (50) with lower ends (52) and upper ends (54), the lower ends being pivotably coupled to the forward positioning section, the upper ends adapted to be pivoted to an increased diameter, the lower ends adapted to be pivoted to a decreased diameter, by contact with the ear canal, for abating the passage of fluid medication to above the position enhancer, electrically conductive contacts (58) on each of the imperforate plates adapted to contact each other and close an electrical circuit to illuminate the ON/OFF button (46) to indicate the system is ready for a user to activate the system and drive the piston.

* * * * *